US012751874B2

(12) United States Patent
Tokugi et al.

(10) Patent No.: US 12,751,874 B2
(45) Date of Patent: Oct. 6, 2026

(54) INFORMATION PROVIDING DEVICE

(71) Applicants: PARAMOUNT BED CO., LTD., Tokyo (JP); aba Inc., Funabashi (JP)

(72) Inventors: Kazuya Tokugi, Tokyo (JP); Sho Ito, Tokyo (JP); Daiki Nomiyama, Tokyo (JP); Shohei Sugano, Funabashi (JP); Atsuko Otsuki, Funabashi (JP); Yoshimi Yokosawa, Funabashi (JP)

(73) Assignees: PARAMOUNT BED CO., LTD., Tokyo (JP); ABA INC., Funabashi (JP)

( * ) Notice: Subject to any disclaimer, the term of this patent is extended or adjusted under 35 U.S.C. 154(b) by 587 days.

(21) Appl. No.: 18/032,031

(22) PCT Filed: Dec. 7, 2021

(86) PCT No.: PCT/JP2021/044919
§ 371 (c)(1),
(2) Date: Apr. 14, 2023

(87) PCT Pub. No.: WO2022/131074
PCT Pub. Date: Jun. 23, 2022

(65) Prior Publication Data

US 2023/0381039 A1 Nov. 30, 2023

(30) Foreign Application Priority Data

Dec. 17, 2020 (JP) ................................ 2020-208964

(51) Int. Cl.
*A61G 7/02* (2006.01)
*A61B 5/00* (2006.01)

(52) U.S. Cl.
CPC ................ *A61G 7/02* (2013.01); *A61B 5/002* (2013.01); *A61B 5/4812* (2013.01)

(58) Field of Classification Search
CPC ...... A61G 7/02; A61G 7/05769; A61G 7/015; A61G 2203/12; A61G 2203/30;
(Continued)

(56) References Cited

U.S. PATENT DOCUMENTS 5,341,127 A 8/1994 Smith
9,934,427 B2 * 4/2018 Derenne ............ G08B 21/0476
(Continued)

FOREIGN PATENT DOCUMENTS

CN 105832477 A 8/2016
CN 211156718 U 8/2020
(Continued)

*Primary Examiner* — Fredrick C Conley
(74) *Attorney, Agent, or Firm* — Birch, Stewart, Kolasch & Birch, LLP

(57) ABSTRACT

An information providing device capable of more adequately providing information regarding excretion is provided. According to one embodiment of the invention, the information providing device includes a processor. The processor acquires a first signal and a second signal. The first signal is obtained from an excretion sensor to detect excretion of a user. The second signal is obtained from a sleep sensor to detect a sleep state of the user. The processor outputs a notification signal for notifying the excretion when the first signal includes first information corresponding to a fact that the user is excreting, and the second signal includes second information corresponding to a fact that the user is awake. The processor does not output the notification signal in a first mode when the first signal includes the first information and, the second signal does not include the second information.

14 Claims, 14 Drawing Sheets

(58) Field of Classification Search
CPC .... A61G 2203/44; A61G 7/05; A61B 5/4812; A61B 5/0205; A61B 5/1115; A61B 5/207; A61B 5/4809; A61B 5/6892; A61B 5/4261; A61B 5/6808; A47C 20/08; A47C 21/06
See application file for complete search history.

(56) References Cited

U.S. PATENT DOCUMENTS

2006/0162074 A1* 7/2006 Bader .................. A47C 27/082 600/595
2009/0151074 A1* 6/2009 Nagaoka ................ A47C 20/08 5/616
2010/0101022 A1* 4/2010 Riley ..................... A61B 5/024 702/19
2011/0092890 A1* 4/2011 Stryker .................. A61G 7/057 604/23
2014/0266736 A1* 9/2014 Cretu-Petra .......... A61B 5/6808 340/573.5
2014/0276504 A1* 9/2014 Heil ........................ A61F 13/42 604/361
2015/0109442 A1* 4/2015 Derenne ................ H04N 7/185 348/143
2015/0212034 A1 7/2015 Ansley
2016/0022218 A1* 1/2016 Hayes .................. A61B 5/7275 600/595
2017/0143565 A1* 5/2017 Childs .................. A61G 7/0524
2018/0242918 A1* 8/2018 Kogure .................. G08B 25/10
2019/0072508 A1* 3/2019 Yoshida .................... A61F 5/48
2020/0060599 A1 2/2020 Monson et al.
2020/0253528 A1 8/2020 Harmeyer
2020/0305256 A1 9/2020 Tachikawa et al.
2021/0298682 A1 9/2021 Hayes et al.
2025/0285744 A1* 9/2025 Durlach ................ A61B 5/1117

FOREIGN PATENT DOCUMENTS

JP 7-34821 U 6/1995
JP 2000-245779 A 9/2000
JP 2018-147104 A 9/2018
JP 2019-3451 A 1/2019

* cited by examiner

INFORMATION PROVIDING DEVICE

TECHNICAL FIELD

Embodiments of the invention relates to an information providing device.

BACKGROUND ART

For example, excretion is detected by sampling the air in the bed. It is desirable to provide more appropriate information on excretion.

PRIOR ART DOCUMENT

Patent Document

[Patent Document 1] JP 2000-245779A

SUMMARY OF INVENTION

Problem to be Solved by Invention

The embodiments of the invention provide an information providing device capable of providing more appropriate information on excretion.

Means for Solving Problem

According to one embodiment of the invention, an information providing device includes a processor. The processor acquires a first signal and a second signal. The first signal is obtained from an excretion sensor to detect excretion of a user. The second signal is obtained from a sleep sensor to detect a sleep state of the user. The processor outputs a notification signal for notifying the excretion when the first signal includes first information corresponding to a fact that the user is excreting, and the second signal includes second information corresponding to a fact that the user is awake. The processor does not output the notification signal in a first mode when the first signal includes the first information and, the second signal does not include the second information.

Effect of Invention

The embodiments of the invention can provide an information providing device capable of providing more appropriate information on excretion.

EMBODIMENTS OF INVENTION

Figure 1:
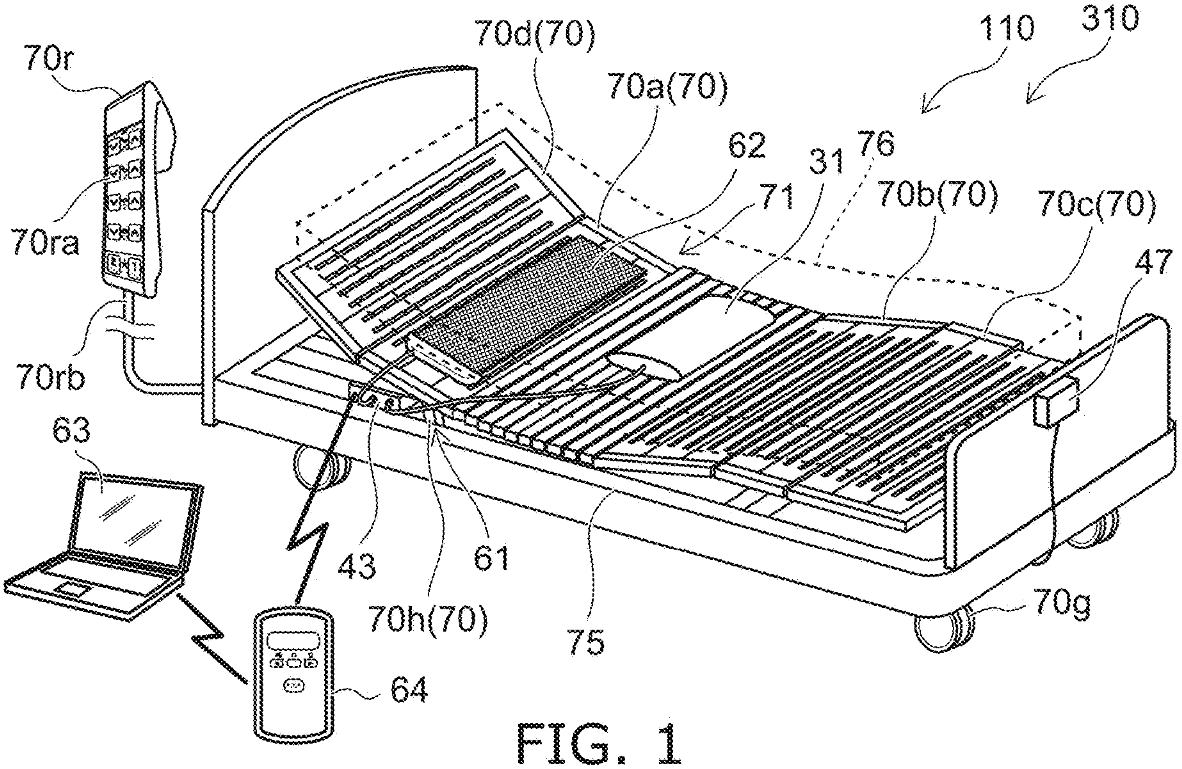
FIG. 1 is a schematic perspective view illustrating an information providing device and a motorized furniture according to a first embodiment.

Embodiments of the invention are described below with reference to the accompanying drawings.

The drawings are schematic and conceptual; and the relationships between the thickness and width of portions, the proportions of sizes among portions, etc., are not necessarily the same as the actual values. The dimensions and proportions may be illustrated differently among drawings, even for identical portions.

In the specification and drawings, components similar to those described previously or illustrated in an antecedent drawing are marked with like reference numerals, and a detailed description is omitted as appropriate.

First Embodiment

FIG. 1 is a schematic perspective view illustrating an information providing device and a motorized furniture according to a first embodiment.

An information providing device 110 according to the embodiment provides, for example, information on excretion of a user (subject). The user uses a motorized furniture 310, for example. In this example, the motorized furniture 310 is a motorized bed.

The motorized furniture 310 is used, for example, in hospitals or nursing homes. The motorized furniture 310 may be used at home or the like.

The motorized furniture 310 includes, for example, a bottom 71 and a mattress 76. In FIG. 1, the mattress 76 is drawn in dashed lines and is shown in perspective for clarity.

The bottom 71 is provided on a frame 75 in the motorized furniture 310. The mattress 76 is provided on the bottom 71. The user lies on the mattress 76. In this example, casters 70*g* are provided under the frame 75. The casters 70*g* may be omitted and changed to "legs".

In this example, the bottom 71 includes a movable part 70. The movable part 70 includes, for example, a back bottom 70*a* (back section), a knee bottom 70*b* (upper leg section), a leg bottom 70*c* (lower leg section), and a height change part 70*h*. The height change part 70*h* is, for example, a bed elevator. As in the example of FIG. 1, the movable part 70 may further include a head bottom 70*d* (head section). A plurality of portions (the back bottom 70*a*, the knee bottom 70*b*, the leg bottom 70*c*, and the head bottom 70*d*) included in the bottom 71 can change their angles relative to each other.

The motorized furniture 310 is provided with a control device 70*r*. The control device 70*r* can control the movable part 70 of the motorized furniture 310 and the like. The control device 70*r* is, for example, a remote controller (remote control) for the motorized furniture 310. The control device 70*r* is, for example, a hand switch.

The control device 70*r* is provided with a user interface device 70*ra* (buttons, touch panel, or the like). The user interface device 70*ra* receives manipulation by the user or the like (the user, the user's caregiver, or the like). For example, the movable part 70 and the like are controlled by the user or the like manipulating the user interface device 70*ra*.

In this example, a processor 43 is provided. The control device 70*r* is connected to the processor 43 by a cable 70*rb*. Actuators and the like operate under the control of the processor 43. The operation of the actuator causes the movable part 70 to operate. In the embodiment, the actuator may function as a bed-departure sensor 61.

In this example, a user interface device 47 is provided. The user interface device 47 may display, for example, the state of the bed (for example, the angle and height of the bottom). The user interface device 47 may display the state of the user and the like. For the user interface device 47, for example, the contents of Japanese Patent Application No. 2017-173364 (title of invention: control device and motorized bed, filing date: Sep. 8, 2017) are cited. This patent application is incorporated in its entirety by this reference.

The processor 43 described above may be included in the information providing device 110, for example. The processor 43 includes, for example, an electric circuit (such as an IC).

The processor 43 acquires a signal (first signal) obtained from an excretion sensor 31 and a signal (second signal) obtained from a sleep sensor 62.

The excretion sensor 31 detects excretion of the user of the motorized furniture 310. In this example, the excretion sensor 31 is placed on the mattress 76 of the motorized furniture 310. The user's buttocks (for example, a diaper) are positioned on the excretion sensor 31. The excretion sensor 31 detects, for example, an odor associated with excretion of the user. Thereby, the excretion sensor 31 detects the user's excretion (for example, at least one of feces and urine). The information providing device 110 may include an excretion sensor 31.

The sleep sensor 62 detects a sleep state of the user. In this example, the sleep sensor 62 is provided between the bottom 71 and the mattress 76. The sleep sensor 62 detects, for example, force (for example, vibration) based on body movement of the user. For example, the sleep sensor 62 detects forces (such as vibrations) based on the user's heartbeat and breathing.

For example, at least one of heart rate per unit time and respiratory rate per unit time may be detected. The sleep sensor 62 can detect whether the user is in a sleep state or in an awake state. The sleep sensor 62 may detect whether the user is on the motorized furniture 310 (for example, bed) (in bed) or not (out of bed). As the sleep sensor 62, for example, the contents of U.S. patent application Ser. No. 15/757,495 (title of invention: ABNORMALITY NOTIFICATION SYSTEM, ABNORMALITY NOTIFICATION METHOD, AND PROGRAM, filing date: Mar. 5, 2018), U.S. patent application Ser. No. 15/757,484 (title of invention: BIO-INFORMATION OUTPUT DEVICE, BIO-INFORMATION OUTPUT METHOD AND PROGRAM, filing date: Mar. 5, 2018) are cited. These patent applications are incorporated in their entirety by this reference.

The processor 43 outputs a notification signal for notifying excretion when the first signal (the signal obtained from the excretion sensor 31) includes "first information corresponding to the fact that the user is excreting" and the second signal (the signal obtained from the sleep sensor 62) includes "second information corresponding to the fact that the user is awake". The first information may be information corresponding to "the user is excreting feces". The first information may be information corresponding to "the user is excreting at least one of feces and urine".

For example, the notification signal is sent to a communicator 64 provided in the information providing device 110, for example. Communication between the processor 43 and the communicator 64 is performed by any wired or wireless method.

In one example, the notification signal is provided to a server 63 or the like. The server 63 accumulates detection results, for example. The server 63 may analyze the detection results. The server 63 may provide detection results and analysis results to other communication devices.

In one example, the notification signal is provided to a portable terminal or the like owned by a user's caregiver or the like. For example, the notification signal may be provided from the communicator 64 to a portable terminal or the like owned by a parent or the like. The notification signal may be provided from the server 63 to the portable terminal or the like owned by a parent or the like.

The caregiver who receives the notification signal changes the user's diaper. If the excretion sensor is not used, the caregiver, for example, needs to periodically check the user's excretion state. This places a heavy burden on caregivers.

In the embodiment, excretion is detected by the excretion sensor 31, and the caregiver receives the notification signal based on the detection result and changes the diaper. Therefore, the burden on caregivers can be reduced.

In the embodiment, the notification signal is output when the first signal includes "first information corresponding to the fact that the user is excreting" and the second signal includes "second information corresponding to the fact that the user is awake." Since the user is awake, even if the caregiver who receives the notification signal changes the diaper, it is possible to prevent the user's sleep from being disturbed.

Furthermore, in the embodiment, the processor 43 may have multiple operation modes.

For example, in the first mode, the processor 43 does not output the notification signal when the first signal (the signal obtained from the excretion sensor 31) includes first the information (information corresponding to the fact that the user is excreting), and the second signal (the signal obtained from the sleep sensor 62) does not include the second information (information corresponding to the fact that the user is awake). For example, even if the user is excreting, the notification signal is not output when the user is not awake (for example, sleeping).

If the user is asleep when the caregiver changes the diaper, the diaper change disturbs the user's sleep. In the embodiment, no notification signal is output when the user is not awake (e.g., sleeping). Therefore, it is possible to prevent the user's sleep from being disturbed.

Several examples of the processor 43 will be described below.

Figure 2A:
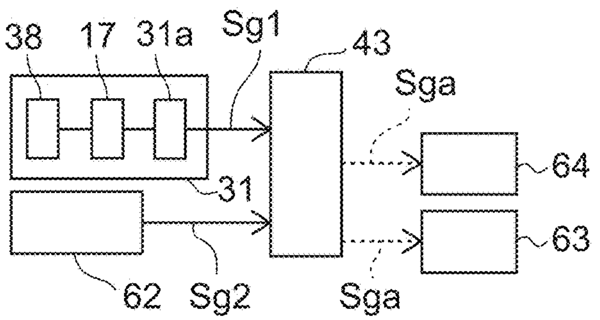
FIG. 2A to FIG. 2C are schematic views illustrating the information providing device and the motorized furniture according to a first embodiment.
Figure 2B:
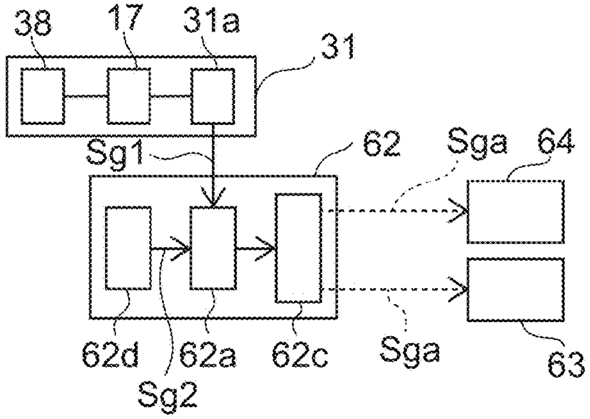
Figure 2C:
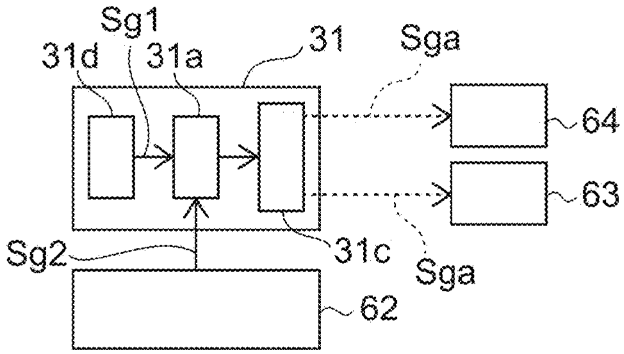

FIG. 2A to FIG. 2C are schematic views illustrating the information providing device and the motorized furniture according to a first embodiment.

As shown in FIG. 2A, the processor 43 may be provided separately from the excretion sensor 31 and the sleep sensor 62. For example, the first signal Sg1 from the excretion sensor 31 is supplied to the processor 43. For example, the second signal Sg2 from the sleep sensor 62 is supplied to the processor 43. A notification signal Sga is output from the processor 43. The notification signal Sga is supplied to at least one of the communicator 64 and the server 63, for example.

In this example, the excretion sensor 31 includes a gas collector 38, an odor sensor 17 and a circuit 31*a*. The gas collector 38 collects gas. The gas includes, for example, odor associated with excretion. The gas collected by the gas collector 38 is supplied to the odor sensor 17. The odor sensor 17 detects, for example, the odor associated with excretion. The detection result is provided to the circuit 31*a*. For example, the first signal Sg1 is output from the circuit 31*a*.

As shown in FIG. 2B, for example, at least a part of the functions of the processor 43 may be performed inside the sleep sensor 62. For example, the sleep sensor 62 includes a circuit 62*a*, a communicator 62*c* and a sensor 62*d*. The sensor 62*d* detects body movements of the user (including, for example, heartbeat and respiration). The detection result (second signal Sg2) is supplied from the sensor 62*d* to the circuit 62*a*. The circuit 62*a* detects, for example, the user's state (sleep, awake, etc.) based on the second signal Sg2. On the other hand, the first signal Sg1 from the excretion sensor 31 is supplied to the circuit 62*a*. The circuit 62*a* performs the above operation based on the first signal Sg1 and the second signal Sg2. The circuit 62*a* functions as the processor 43. A processing result (e.g., notification signal Sga) of the circuit 62*a* (processor 43) is output.

As shown in FIG. 2C, for example, at least a part of the functions of the processor 43 may be performed inside the excretion sensor 31. In this example, the excretion sensor 31 includes the circuit 31*a*, a communicator 31*c* and a sensor 31*d*. The sensor 31*d* detects the odor associated with excretion of the user. The sensor 31*d* includes, for example, the gas collector 38 and the odor sensor 17 (see FIG. 2A).

In addition, at least a part of the operation of the processor 43 may be performed by another device (for example, the server 63 or the like).

Figure 3:
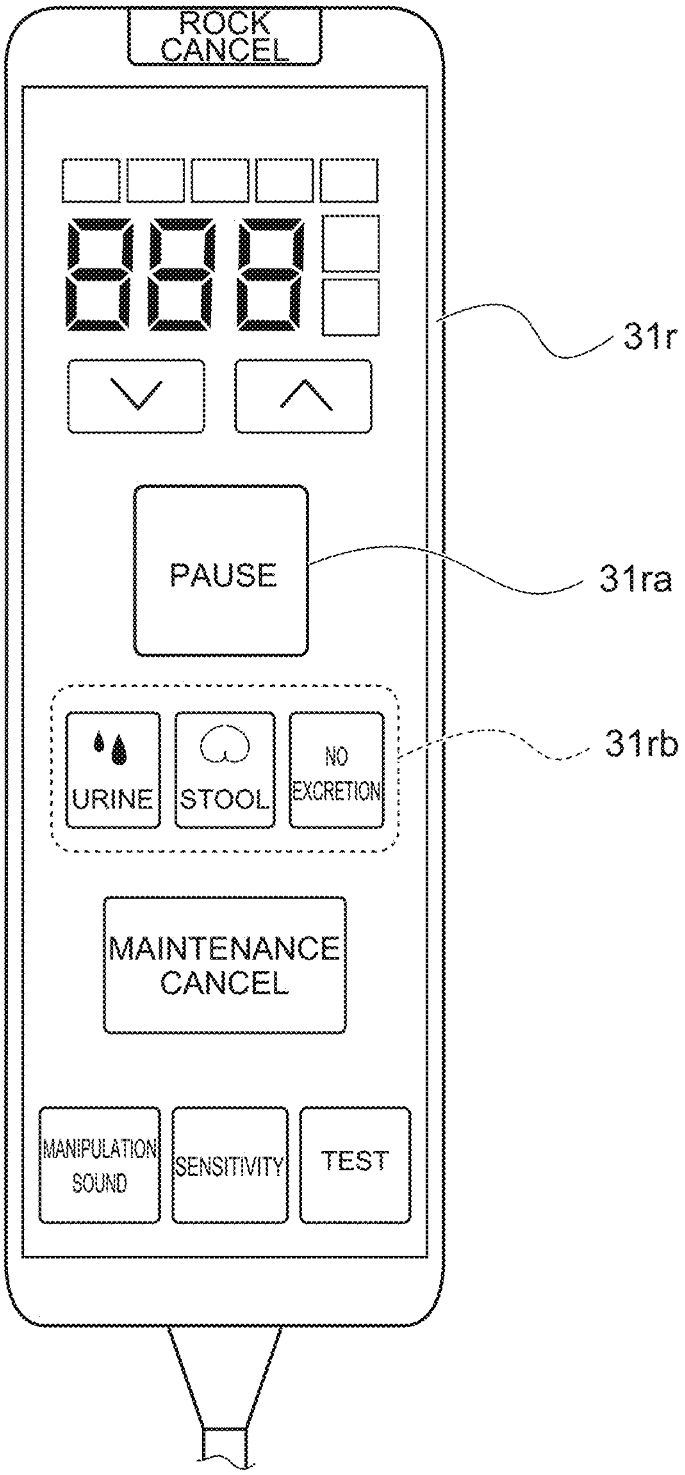
FIG. 3 is a schematic view illustrating a part of an excretion sensor according to the first embodiment.

FIG. 3 is a schematic view illustrating a part of an excretion sensor according to the first embodiment.

The excretion sensor 31 may be provided with an excretion sensor controller 31*r* illustrated in FIG. 3. The excretion sensor controller 31*r* is a remote controller. The excretion sensor controller 31*r* is, for example, a hand switch. The excretion sensor controller 31*r* receives various controls regarding the excretion sensor 31, for example. For example, a "pause" button 31*ra* is provided in the excretion sensor controller 31*r*. For example, when the caregiver who receives the notification signal Sga presses the "pause" button 31*ra*, the transmission of the notification signal Sga is terminated. An "excretion result" button 31*rb* may be provided in the excretion sensor controller 31*r*.

The caregiver can enter the user's actual excretion state (e.g., "urine," "feces (stool)," or "no excretion," etc.). After the "pause" button 31*ra* is pressed, the pause state may be automatically canceled after a certain period of time has passed, and the transmission of the notification signal Sga may be restarted. The transmission of the notification signal Sga may be restarted by, for example, pressing another button (for example, the "excretion result" button 31*rb*) without being limited to this case. For example, the transmission of the notification signal Sga may be restarted when a body movement sensor or the like detects that the diaper has been changed.

For example, when the excretion sensor controller 31*r* pauses or records excretion, the notification display on the server 63 may be deleted. The display of the excretion sensor controller 31*r* may be deleted when the server 63 temporarily stops or records excretion.

As already described, in the information providing device 110 according to the embodiment, multiple operation modes may be performed. Some examples of modes are described below.

Figure 4:
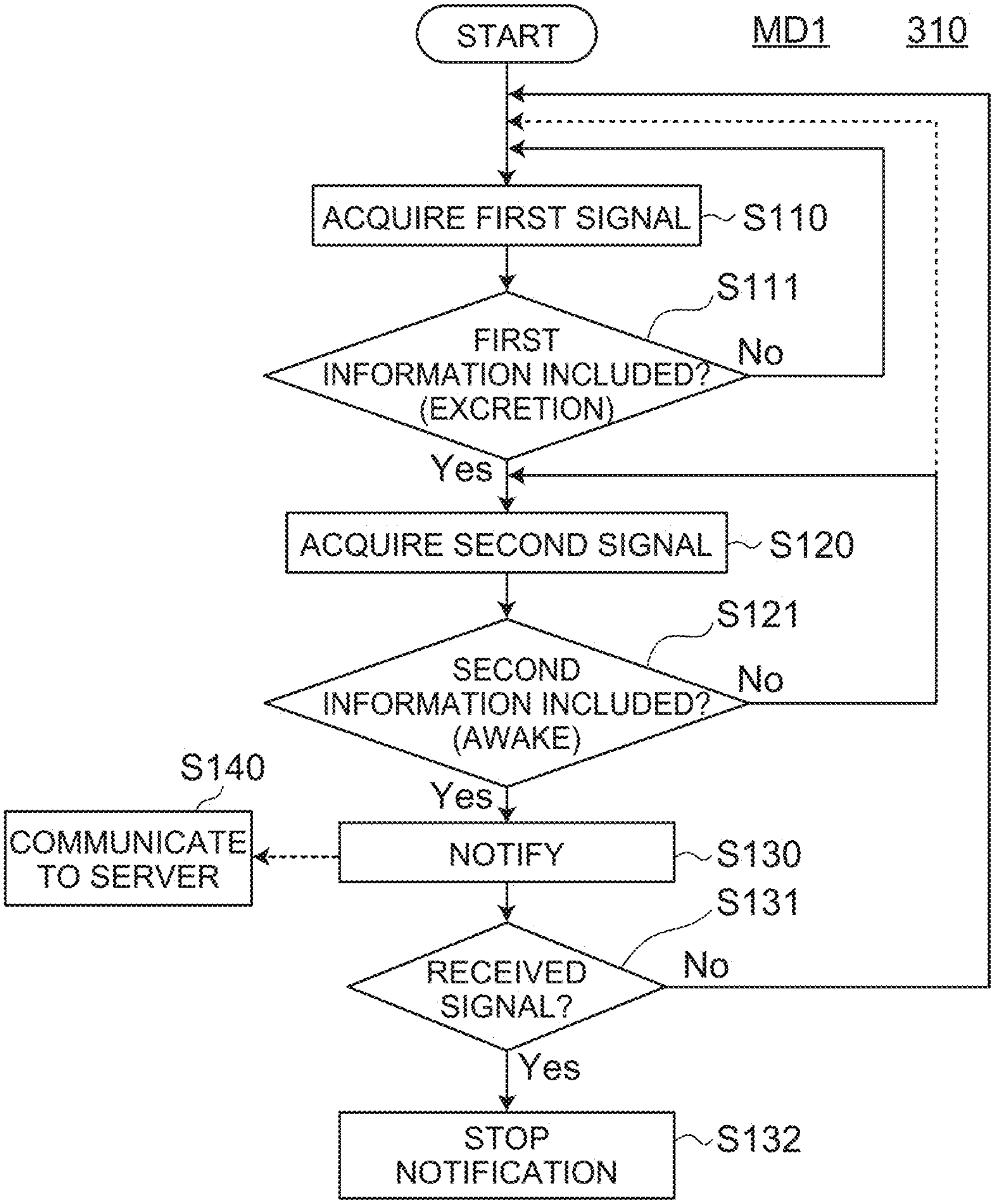
FIG. 4 is a flow chart illustrating the operation of the information providing device according to the first embodiment.

FIG. 4 is a flow chart illustrating the operation of the information providing device according to the first embodiment.

FIG. 4 illustrates a first mode MD1. As already described, at least one of feces and urine may be detected in the first mode MD1. In order to simplify the description, a case where feces is detected in the first mode MD1 will be described below as an example.

In the first mode MD1, the first signal Sg1 is obtained (step S110). Then, it is determined whether or not the first signal Sg1 includes "first information corresponding to the fact that the user is excreting feces" (step S111). When the first signal Sg1 does not include the first information (when there is no feces excretion), the process returns to step S110.

When the first signal Sg1 includes the first information (when there is feces excretion), the second signal Sg2 is acquired (step S120). Then, it is determined whether the second signal Sg2 includes "second information corresponding to the fact that the user is awake" (whether the user is awake or asleep) (step S121). When the second signal Sg2 does not include the second information (when not awakened), the process returns to step S120.

When the second signal Sg2 includes the second information (when the person is awake), the notification signal Sga is output (step S130). The various operations described above are performed by the processor 43, for example. Communication to the server 63 may be performed when the notification signal Sga is output.

For example, the caregiver who receives the notification signal Sga manipulates the "pause" button 31*ra* of the excretion sensor controller 31*r*. Accordingly, it is determined that the notification signal Sga has been received. A signal generated by manipulating the "pause" button 31*ra* becomes a received signal.

Thus, for example, after outputting the notification signal Sga (step S130), it is determined whether or not the received signal indicating that the notification signal has been received has been obtained (step S131). If no received signal is obtained, for example, the process returns to the start or step S110. When the received signal is obtained, the notification signal Sga is stopped. As a result, notification is stopped (step S132).

Thus, the processor 43 does not output the notification signal Sga when the first signal Sg1 includes the first information and the second signal Sg2 does not include the second information in the first mode MD1. In the first mode MD1, the caregiver's burden can be reduced. The user's sleep disturbance can be suppressed.

Figure 5:
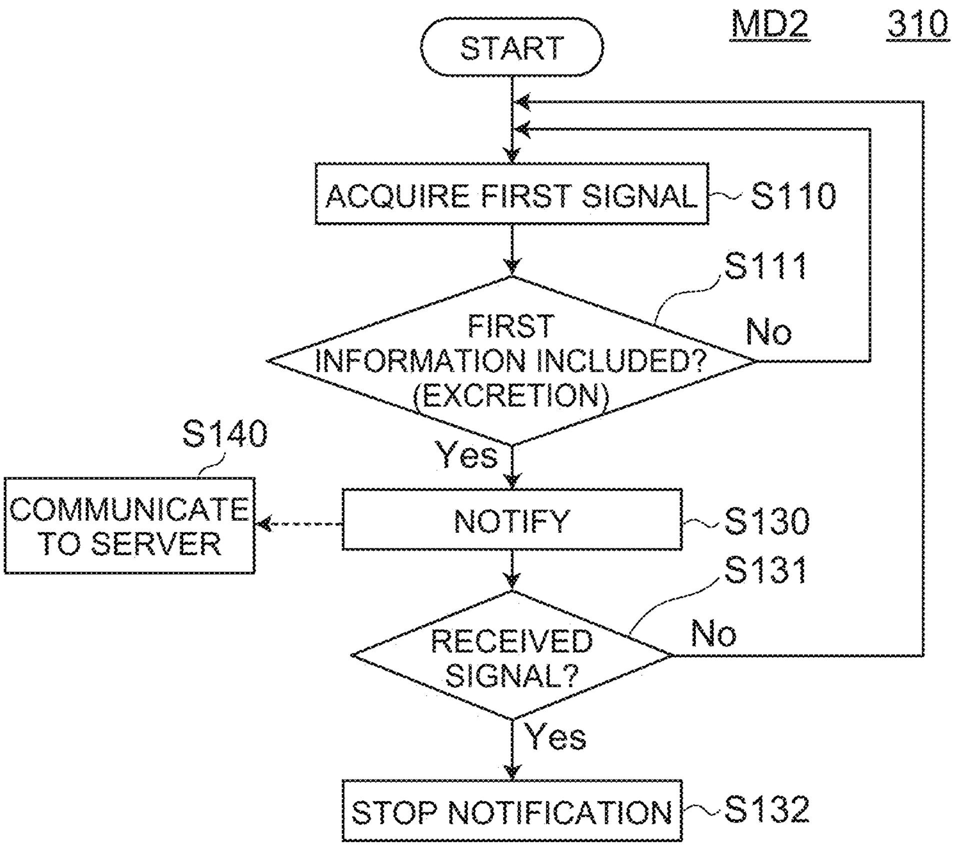
FIG. 5 is a flow chart illustrating the operation of the information providing device according to the first embodiment.

FIG. 5 is a flow chart illustrating the operation of the information providing device according to the first embodiment.

FIG. 5 illustrates a second mode MD2. As already described, at least one of feces and urine may be detected in the second mode MD2. In order to simplify the description, a case where feces is detected in the second mode MD2 will be described below as an example.

As shown in FIG. 5, in the second mode MD2, the processor 43 outputs the notification signal Sga when the first signal Sg1 includes the first information (step S130). In the second mode MD2, regardless of the sleep state of the user, the notification signal Sga is output when the first information (excretion of feces) is detected.

Depending on the user's condition, it may be better to give priority to changing the diaper than disturbing the user's sleep. In such a case, the second mode MD2 is performed.

In another example of the first mode MD1, excretion of feces and/or urine is detected. In this case, in step S111 illustrated in FIG. 4, it is determined whether or not the first signal Sg1 includes "first information corresponding to the fact that the user is excreting at least one of feces and urine". Then, each step after step S111 is performed.

In another example of the second mode MD2, excretion of feces and/or urine is detected. In this case, in step S111 illustrated in FIG. 5, it is determined whether or not the first signal Sg1 includes "first information corresponding to the fact that the user is excreting at least one of feces and urine". Then, each step after step S111 is performed.

In another example of the first mode MD1, urine excretion is detected. In this case, in step S111 illustrated in FIG. 4, it is determined whether or not the first signal Sg1 includes "first information corresponding to the fact that the user is urinating". Then, each step after step S111 is performed.

In another example of the second mode MD2, at least some urine is detected. In this case, in step S111 illustrated in FIG. 5, it is determined whether or not the first signal Sg1 includes "first information corresponding to the fact that the user is urinating". Then, each step after step S111 is performed.

In one example, even if urine is excreted, the notification signal Sga is not output when the user is in the sleep state. Therefore, it is possible to prevent the sleep of the user from being disturbed by changing the diaper.

Depending on the user's condition, it may be better to distinguish between excretion of feces and excretion of urine. There are cases where the user's sleep disturbance is prioritized and cases where it is not prioritized. In such a case, the first information may be set appropriately to switch the operation.

For example, in the case of a person who urinates a large amount, it is preferable to change the diaper even if the urine is only excreted. For example, urine excretion can be quickly detected by determining whether the first signal Sg1 includes "first information corresponding to the fact that the user is excreting urine".

On the other hand, when the frequency of excreting feces is lower than the frequency of urine, for example, the frequency of diaper changes is reduced by determining whether or not the first signal Sg1 includes "first information corresponding to the fact that the user is excreting feces". For example, compared to detecting both feces and urine, the burden on the user can be reduced.

When detecting at least one of feces and urine, when detecting feces, when detecting urine, and when detecting feces and urine, for example, it is easy to grasp the excretion cycle. For example, data of excretion results on multiple days may be accumulated. Based on the accumulated data, a time period in which the probability of excretion is high may be calculated. A time period when the probability of excretion is high includes, for example, at least one of the time of excretion and the time when excretion is finished. The calculated time period may be displayed. The display is performed by, for example, a table or a diagram. A caregiver or the like can recognize this display. For example, it is possible to establish a regular diaper changing plan that is more suitable for the user (cared person). Efficient care can be provided when the caregiver cares for multiple users (care recipients). The caregiver can start changing diapers during a period when the probability of excretion is high. For example, it is possible to reduce the probability of not changing a diaper because there is no excretion when the work for diaper changing is performed. Efficiency of diaper changing work can be improved.

The above modes may be changed according to the user's condition. For example, in a laxative-administered user, both feces and urine are initially detected. Thereafter, by detecting that the user is becoming normal, for example, only feces may be detected.

The setting for switching the mode may be performed by the excretion sensor controller 31*r*, for example. The setting for switching modes may be performed by the server 63, for example.

The various types of processing described above are performed, for example, by the processor 43. The order of some of the above steps may be interchanged within the technically possible range, and may be performed simultaneously. For example, the order of steps S110 and S120 described above is arbitrary. At least some of these steps may be performed simultaneously.

Second Embodiment

Figure 6:
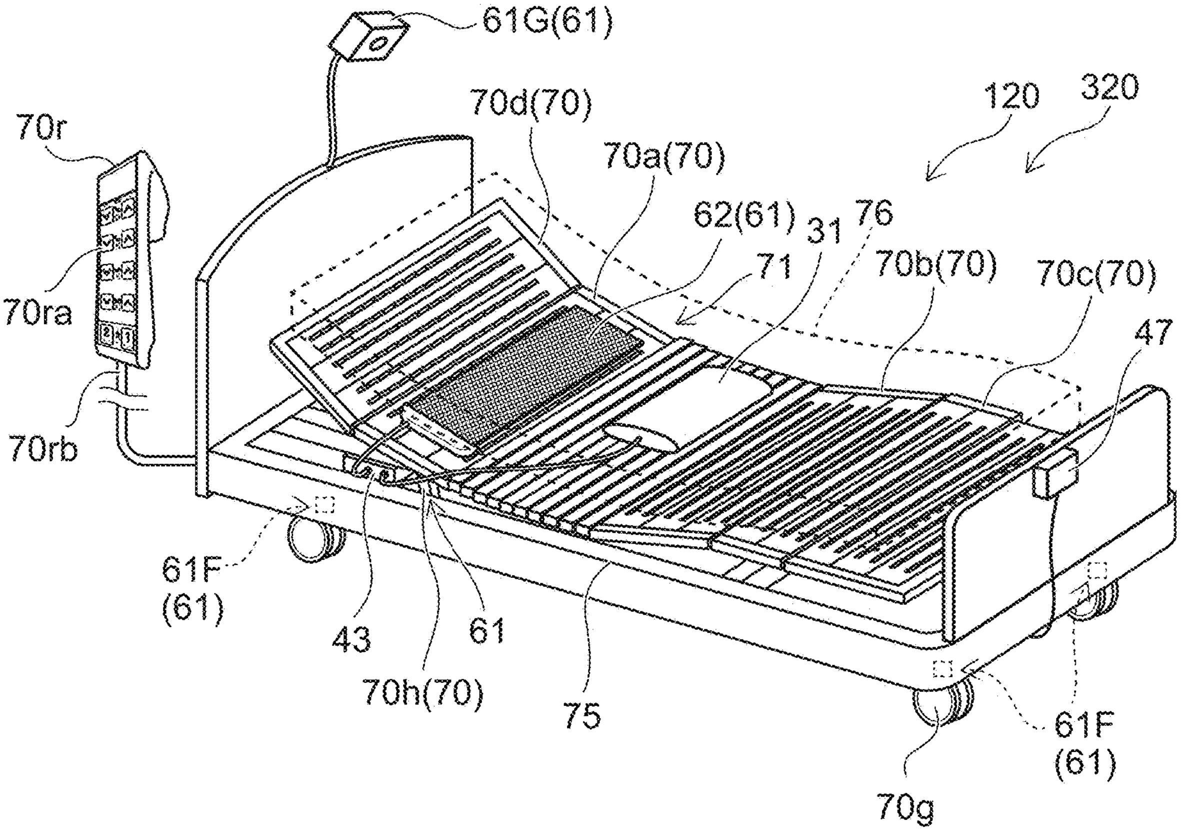
FIG. 6 is a schematic perspective view illustrating an information providing device and a motorized furniture according to a second embodiment.

FIG. 6 is a schematic perspective view illustrating an information providing device and a motorized furniture according to a second embodiment.

In an information providing device 120 and a motorized furniture 320 according to the embodiment, the processor 43 acquires the first signal Sg1 obtained from the excretion sensor 31 that detects the user's excretion, and the second signal Sg2 obtained from the bed-departure sensor 61 that detects the user's bed-departure. The notification signal Sga is output based on these signals. The configuration described in relation to the first embodiment is applied to the excretion sensor 31. An example of the bed-departure sensor 61 will be described below.

As shown in FIG. 6, in one example of the bed-departure sensor 61, the bed-departure sensor 61 is provided in the actuator of the movable part 70. For example, by using an actuator with a load sensor, movement of the movable part 70 (for example, the bottom 71, etc.) is controlled. Then, the load is detected by the load sensor of the actuator. Whether or not the user is on the motorized furniture 320 can be detected by detecting the load.

In addition, the sleep sensor 62 may function as the bed-departure sensor 61. For example, the sleep sensor 62 detects the force according to the body movement of the user. When the user is not on the motorized furniture 320, no force (vibration or the like) based on body movement is detected. Therefore, the sleep sensor 62 can also detect whether the user is on the motorized furniture 320.

A load sensor 61F may be provided as the bed-departure sensor 61. The load sensor 61F is provided, for example, above the casters 70*g* of the bed. Also in this case, it is possible to detect whether the user is on the motorized furniture 320 by the load sensor 61F.

As the bed-departure sensor 61, an image sensor 61G may be provided. Also in this case, the image sensor 61G can detect whether the user is on the motorized furniture 320 or not. In addition, an infrared sensor or the like may be provided as the bed-departure sensor 61.

In the embodiment, the processor 43 outputs the notification signal Sga when the first signal Sg1 (signal from the excretion sensor 31) includes "first information indicating that the user is excreting", and the second signal Sg2 (signal from the bed-departure sensor 61) includes "information that the user is on the bed (motorized furniture 320)". The notification signal Sga is a signal for notifying excretion.

In the embodiment, the processor 43 does not output the notification signal Sga when the first signal Sg1 includes the first information and the second signal Sg2 includes "information that the user is bed-departing."

For example, even when the user is out of bed, the excretion sensor 31 may include "first information indicating that the user is excreting". For example, the excretion sensor 31 may detect odors caused by causes of odors other than excretion (food, perfume, etc.). In this case, the "first information indicating that the user is excreting" may be erroneously included in the first signal Sg1. At this time, if the user is not in bed, the notification signal Sga is not output. As a result, it is possible to suppress the output of an erroneous notification signal Sga. For example, the burden on nurses can be reduced.

In one example, the first information includes "the user is excreting at least one of feces and urine". In another example, the first information includes "the user is excreting feces." In another example, the first information includes "the user is urinating".

Figure 7:
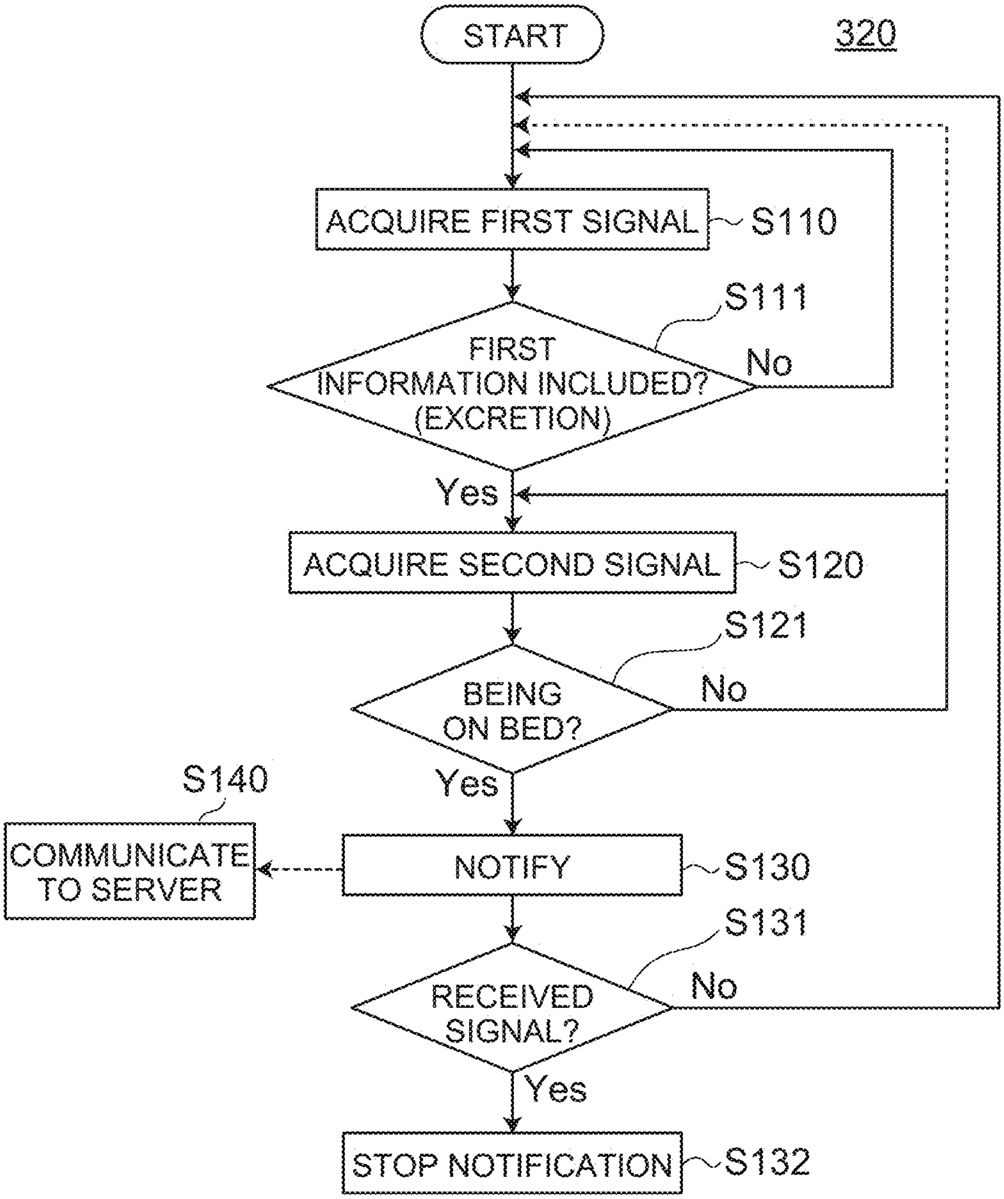
FIG. 7 is a flow chart illustrating the operation of the information providing device according to the second embodiment.

FIG. 7 is a flow chart illustrating the operation of the information providing device according to the second embodiment.

As shown in FIG. 7, the first signal Sg1 is obtained (step S110). Then, it is determined whether or not the first signal Sg1 includes "first information indicating that the user is excreting" (step S111). When the first signal Sg1 does not include the first information (when there is no excretion), the process returns to step S110.

When the first signal Sg1 includes the first information (excretion state), the second signal Sg2 is obtained (step S120). Then, it is determined whether or not the second signal Sg2 includes "information indicating that the user is in bed" (step S121). When the second signal Sg2 does not include the second information (not in bed), the process returns to step S120.

When the second signal Sg2 includes the second information (when in bed), the notification signal Sga is output (step S130). The various operations described above are performed by the processor 43, for example. Communication to the server 63 may be performed when the notification signal Sga is output.

The processor 43 does not output the notification signal Sga when the first signal Sg1 includes the first information (excretion state) and the second signal Sg2 includes "information that the user is out of bed" (step S121). As a result, it is possible to suppress the output of an erroneous notification signal Sga. For example, the burden on nurses is reduced.

Third Embodiment

Figure 8:
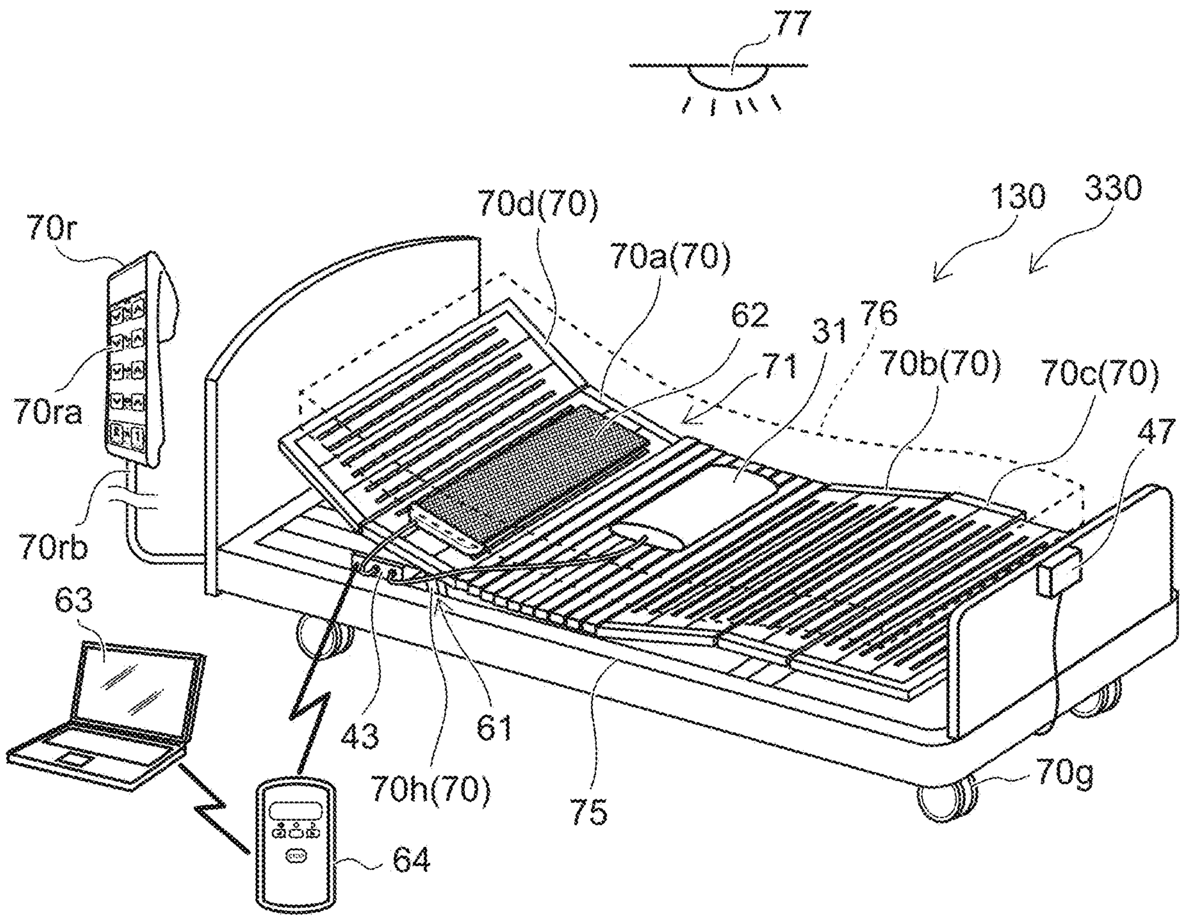
FIG. 8 is a schematic perspective view illustrating an information providing device and a motorized furniture according to a third embodiment.

FIG. 8 is a schematic perspective view illustrating an information providing device and a motorized furniture according to a third embodiment.

In an information providing device 130 and a motorized furniture 330 according to the embodiment, other devices are controlled based on the detection result of the user's excretion.

Other device is, for example, the motorized furniture 330 (for example, a motorized bed) used by a user. Other device may be, for example, an air mattress (described later) of the motorized furniture 330 used by the user. Other device may be lighting 77, for example.

As already described, for example, the notification signal Sga is transmitted (output) based on the detection result of the excretion sensor 31 that detects excretion of the user. Then, as already described, a received signal corresponding to the reception of the transmitted notification signal Sga is transmitted from, for example, the excretion sensor controller 31*r*.

The processor 43 according to the embodiment operates the device for the user when receiving the received signal.

Figure 9:
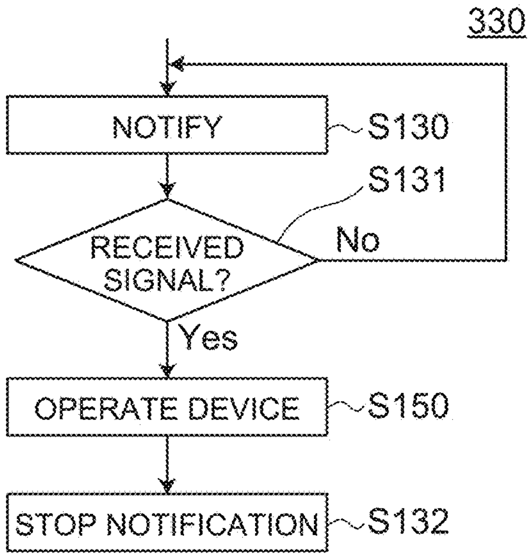
FIG. 9 is a flow chart illustrating the operation of the information providing device and the motorized furniture according to the third embodiment.

FIG. 9 is a flow chart illustrating the operation of the information providing device and the motorized furniture according to the third embodiment.

As shown in FIG. 9, the notification signal Sga is transmitted (output) (step S130). It is determined whether or not the received signal corresponding to the reception of the notification signal Sga has been acquired (step S131). If the received signal is not acquired, the process returns to the start.

When the received signal is acquired, the device is operated (step S150). Then, the transmission (output) of the notification signal Sga is stopped (step S132). In the above, the order of multiple steps is arbitrary. At least some of the multiple steps may be performed simultaneously.

For example, the caregiver changes a diaper when excretion is detected. In the embodiment, various devices are controlled to facilitate diaper changes. As a result, the burden on caregivers can be reduced. Since the diaper can be changed quickly, better service can be provided to the user.

In the embodiment, the device is operated when the received signal is acquired. For example, the received signal is input by the caregiver at the user's side. The caregiver is near the user when inputting the received signal. As a result, erroneous operation can be suppressed. If safety can be ensured, other devices may be controlled based on the first signal Sg1 obtained from the excretion sensor 31 that detects excretion of the user.

For example, if the above device includes the lighting 77, the processor 43 may brighten the lighting 77 when the first signal Sg1 includes the first information.

Some examples of devices are described below.

Figure 10A:
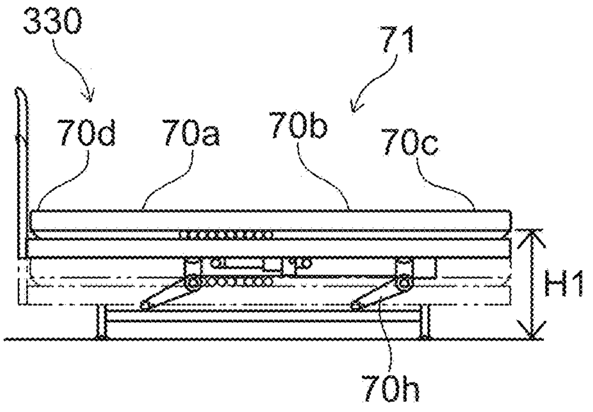
FIG. 10A and FIG. 10B are schematic views illustrating the operation of the motorized furniture according to the third embodiment.
Figure 10B:
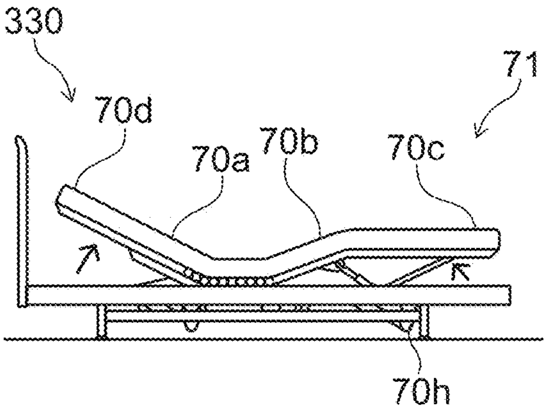

FIG. 10A and FIG. 10B are schematic views illustrating the operation of the motorized furniture according to the third embodiment.

As shown in FIGS. 10A and 10B, as bottoms 71, back bottoms 70*a*, knee bottoms 70*b*, leg bottoms 70*c*, head bottoms 70*d*, and the like are provided. The height change part 70*h* is provided. For example, there are a state where the multiple bottoms 71 are inclined as shown in FIG. 10B, and a flat state shown in FIG. 10A. Then, as shown in FIG. 10A, a distance (height H1) between the bottom 71 and the floor can be changed. In the flat state, diaper change is easy. When the bottom 71 is high, it becomes easier to change diapers.

For example, the processor 43 raises the height of the bottom 71 of the motorized bed (motorized furniture 330) when receiving the received signal. This makes it easier to change diapers.

For example, the processor 43 flattens the bottom 71 of the motorized bed (motorized furniture 330) when receiving the received signal. This facilitates diaper changes.

The processor 43 may raise the height of the bottom 71 when the first signal Sg1 includes the first information (during excretion). The processor 43 may flatten the bottom 71 when the first signal Sg1 includes the first information. In the embodiment, the state in which the bottom 71 is flat is, for example, a "flat" state that can be created by the control device 70*r*.

Figure 11:
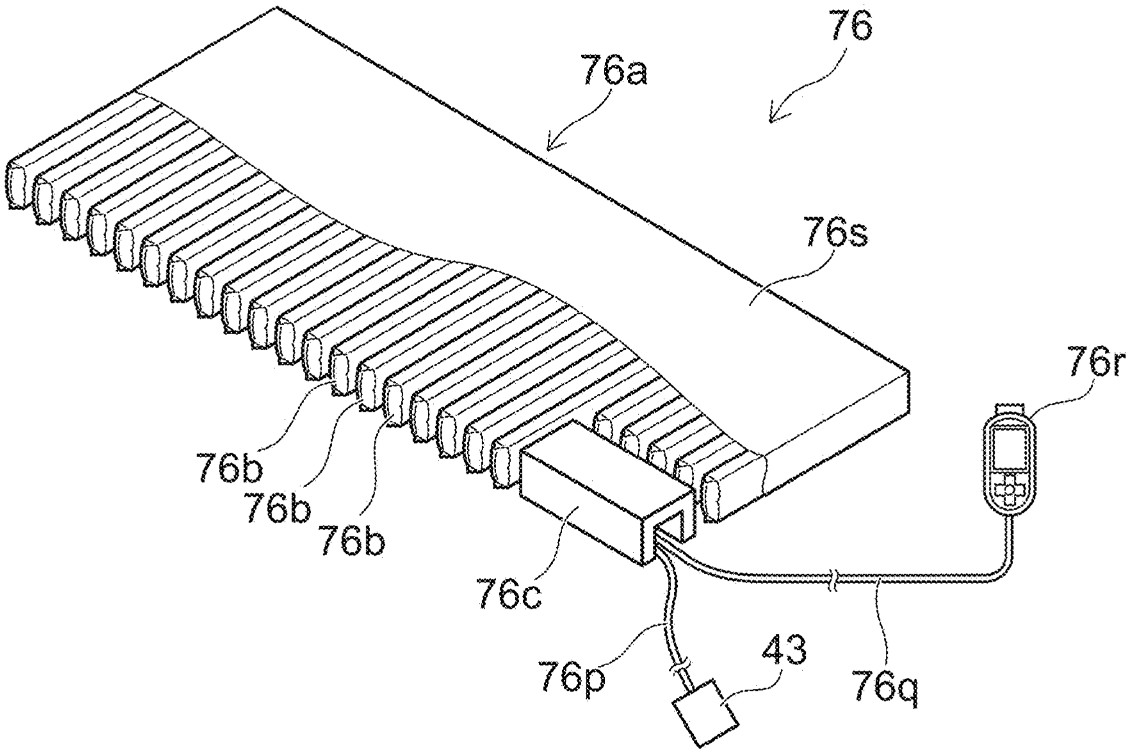
FIG. 11 is a schematic perspective view illustrating the motorized furniture according to the third embodiment.

FIG. 11 is a schematic perspective view illustrating the motorized furniture according to the third embodiment.

FIG. 11 illustrates an air mattress 76*a* as an example of the mattress 76. In the air mattress 76*a*, multiple air cells 76*b* are provided in a seat 76*s*. Air is supplied from a pump unit 76*c* to the multiple air cells 76*b*. The hardness or shape of the air mattress 76*a* can be changed according to the amount of air. For example, the pump unit 76*c* is provided with an air mattress controller 76*r* (for example, a remote controller). The air mattress controller 76*r* is connected to the pump unit 76*c* by a cable 76*q*. By manipulating the air mattress controller 76*r*, the operation of the pump unit 76*c* is controlled, and the hardness or shape of the air mattress 76*a* can be controlled.

For example, the processor 43 is connected with the pump unit 76*c*. Connections are made by any method, wired or wireless. In this example, a cable 76*p* connects the processor 43 to the pump unit 76*c*.

In the embodiment, if the device includes the air mattress 76*a* for use by the user, the processor 43 stiffens the air mattress 76*a* (e.g., at least the central portion) upon receiving the received signal. This facilitates diaper changes.

The processor 43 may stiffen the air mattress 76*a* (for example, at least the central portion) when the first signal Sg1 includes the first information (during excretion).

In the third embodiment, the processor 43 outputs the notification signal Sga for notifying excretion when the first signal Sg1 includes the first information (when excreting) (step S130). The received signal corresponding to the notification signal Sga is acquired by the processor 43. Safer operation can be performed by operating the device according to the acquisition result of the received signal.

The third embodiment and the first embodiment may be combined and implemented. The third embodiment and the second embodiment may be combined and performed. The first embodiment and the second embodiment may be combined and implemented.

The operation of the device in the third embodiment and the operations in the first mode MD1 and the second mode MD2 in the first embodiment may be combined and performed. For example, after step S131 illustrated in FIG. 4 and FIG. 5, step S150 illustrated in FIG. 9 is performed, and step S132 is performed.

The operation of the device in the third embodiment and the operation in the second embodiment may be combined and performed. For example, after step S131 illustrated in FIG. 7, step S150 illustrated in FIG. 9 is performed, and step S132 is performed.

Fourth Embodiment

Figure 12:
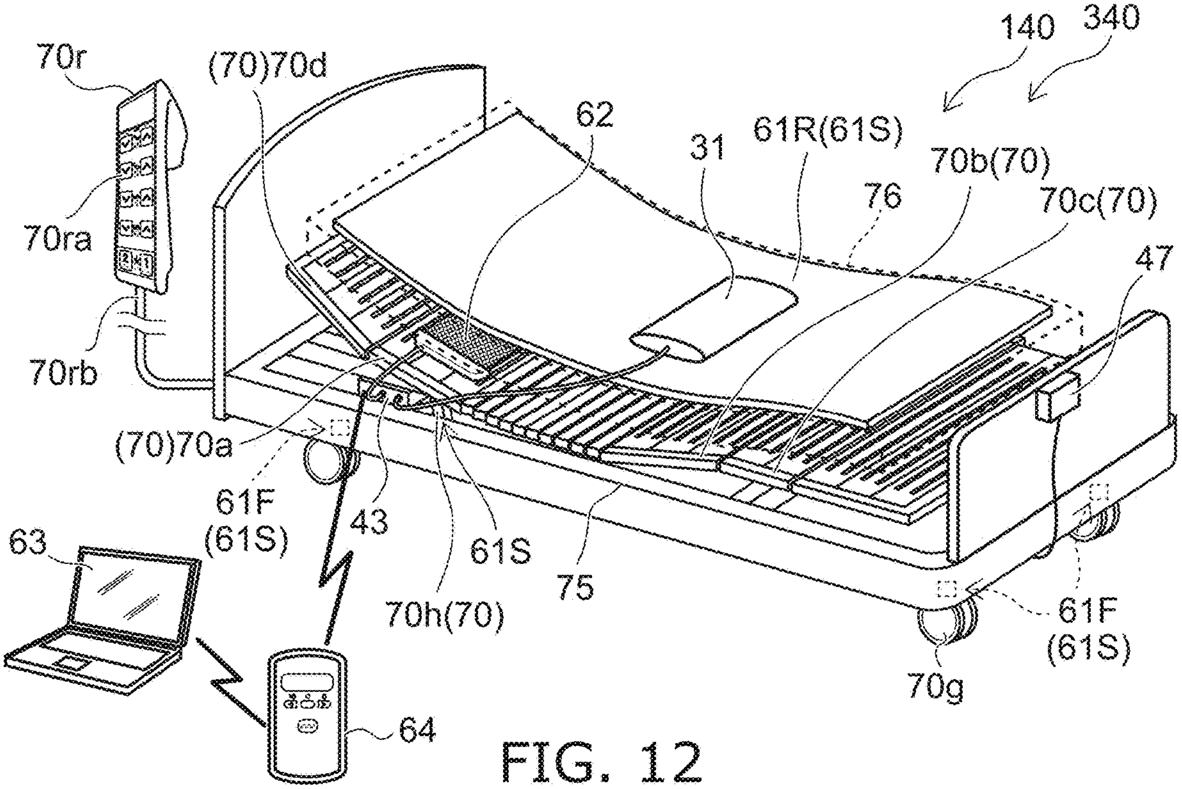
FIG. 12 is a schematic perspective view illustrating an information providing device and a motorized furniture according to a fourth embodiment.

FIG. 12 is a schematic perspective view illustrating an information providing device and a motorized furniture according to a fourth embodiment.

An information providing device 140 and a motorized furniture 340 according to the embodiment are provided with a position sensor 61S that detects the position of the user. For example, a body pressure measurement mat 61R may be used as the position sensor 61S. For example, the load sensor 61F may be used as the position sensor 61S. The position sensor 61S may include a load sensor provided in the actuator of the motorized bed.

The processor 43 acquires a signal obtained from the position sensor 61S that detects the position of the user. When a position of the user is not in a state where excretion is detected by the excretion sensor 31, the processor 43 notifies the state.

For example, the user's buttocks may be away from the proper position of the excretion sensor 31. In this case, excretion may not be detected properly. At this time, the user's position is detected, and if the result is inappropriate, a notification indicating that fact is output. Excretion can thereby be detected more accurately.

Figure 13:
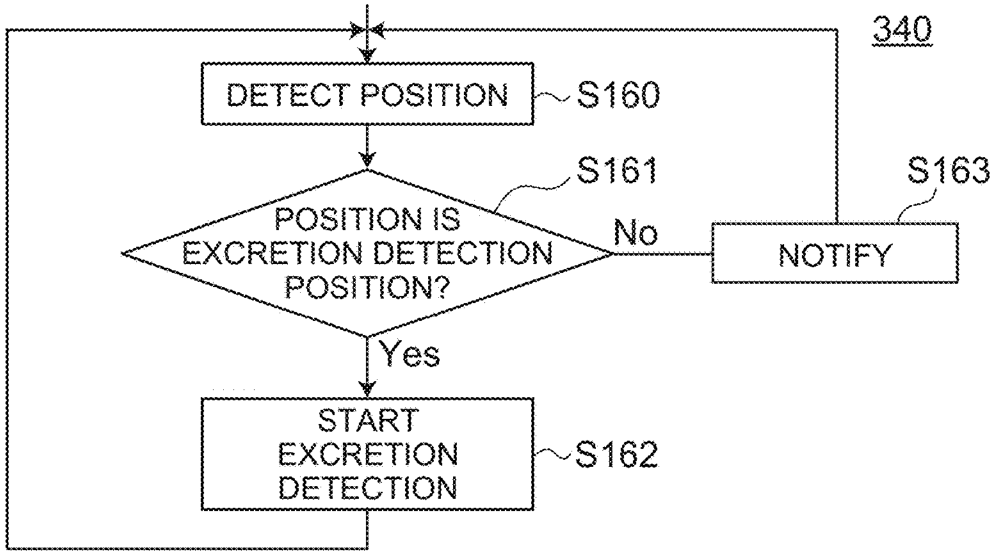
FIG. 13 is a flow chart illustrating the operation of the information providing device and the motorized furniture according to the fourth embodiment.
Figure 14:
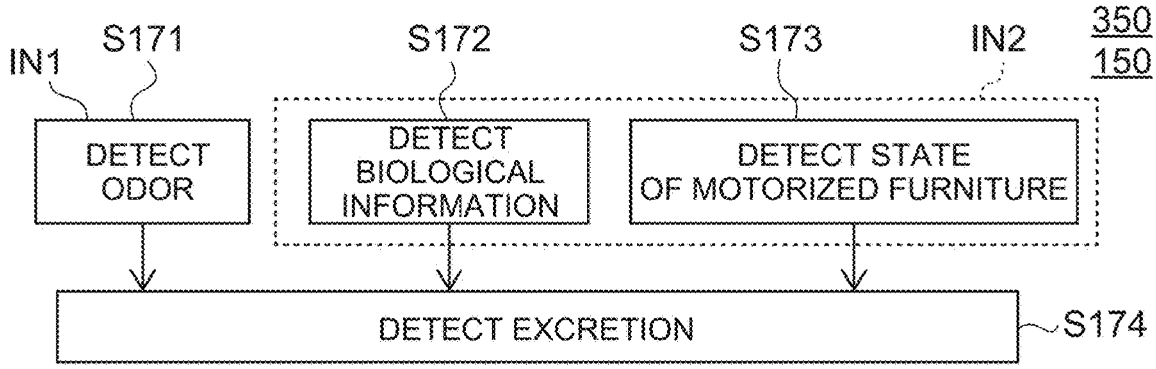
FIG. 14 is a flow chart illustrating the operation of an information providing device and a motorized furniture according to a fifth embodiment.

FIG. 13 is a flow chart illustrating the operation of the information providing device and the motorized furniture according to the fourth embodiment.

As shown in FIG. 13, a signal is acquired from the position sensor 61S that detects the position of the user (step S160).

It is determined whether or not the user is at a position where excretion is detected by the excretion sensor 31 (step S161). If the user's position is not at the position where excretion is detected by the excretion sensor 31, notification is given (step S163). After that, the process returns to step S160.

When the user is at a position where excretion is detected by the excretion sensor 31, detection of excretion is started (step S162). Then, the process returns to step S160. In the embodiment, excretion can be detected more accurately.

Fifth Embodiment

An information providing device 150 and a motorized furniture 350 according to the embodiment are also provided with the processor 43 (see, for example, FIG. 1 and FIG. 2A to FIG. 2C). The processor 43 detects the user's excretion based on first information IN1 and second information IN2. The first information IN1 includes odor detection results obtained from the space around the user. The second information IN2 includes at least one of the user's biological information and the motorized furniture information relating to the state of the motorized furniture used by the user.

For example, an odor is detected (step S171). On the other hand, the biological information of the user is detected (step S172). The state of the motorized furniture is detected (step S173). Then, based on these detection results, excretion of the user is detected (step S174).

The user's biological information can be detected by, for example, the sleep sensor 62 described with reference to FIG. 1. The biological information may be detected by various load sensors or the like. The biological information includes, for example, at least one of sleep/awake of the user, body movement of the user, heart rate of the user, breathing rate of the user, bed-departure of the user, and being in bed of the user.

When the motorized furniture 350 includes the bottom 71, the motorized furniture information includes at least one of the angle of the bottom 71 and the height of the bottom 71.

For example, in the embodiment, whether or not the user excretes is determined based on the first information IN1 and the second information IN2. As a result, excretion can be detected more accurately than, for example, when the determination is made using only the first information IN1.

For example, when the bottom 71 of the motorized furniture 350 is tilted, the odor may be easily detected erroneously. In such a case, determination using the first information IN1 and the second information IN2 makes the detection more accurate.

Sixth Embodiment

Figure 15:
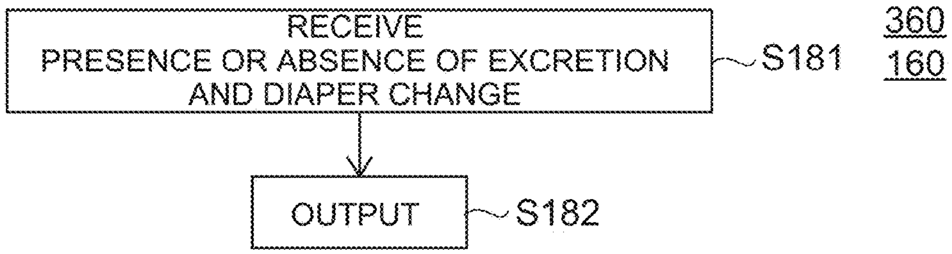
FIG. 15 is a flow chart illustrating the operation of an information providing device and a motorized furniture according to a sixth embodiment.

FIG. 15 is a flow chart illustrating the operation of an information providing device and a motorized furniture according to a sixth embodiment.

In an information providing device 160 and a motorized furniture 360 according to the embodiment, the processor 43 (see, for example, FIG. 1 and FIG. 2A to FIG. 2C) and the excretion sensor controller 31*r* (see FIG. 3) are provided.

The processor 43 can output the notification signal Sga for notifying excretion based on the signal (first signal Sg1) obtained from the excretion sensor 31 that detects the odor from the space around the user. The excretion sensor controller 31*r* can control the operation of the excretion sensor 31.

In the embodiment, the excretion sensor controller 31*r* can receive an input regarding at least one of the presence or absence of excretion and diaper change (step S181). For example, as shown in FIG. 3, an "excretion result" button 31*rb* is provided. The caregiver can enter the user's actual excretion state (e.g., "urine," "feces (stool)," or "no excretion," etc.).

The processor 43 can output the input received by the excretion sensor controller 31*r* (step S182). The input received by the excretion sensor controller 31*r* is provided to the server 63 or the like, for example.

For example, an excretion record is created in the server 63 or the like. For example, the number of used diapers may be recorded. For example, it may be used for inventory management of diapers. In one example, step S181 is performed after step S132 illustrated in FIG. 4 and FIG. 5, for example. In the embodiment, step S181 may, for example, be performed independently of the first mode MD1 and the second mode MD2.

Several examples of the sleep sensor 62 are described below.

Figure 16A:
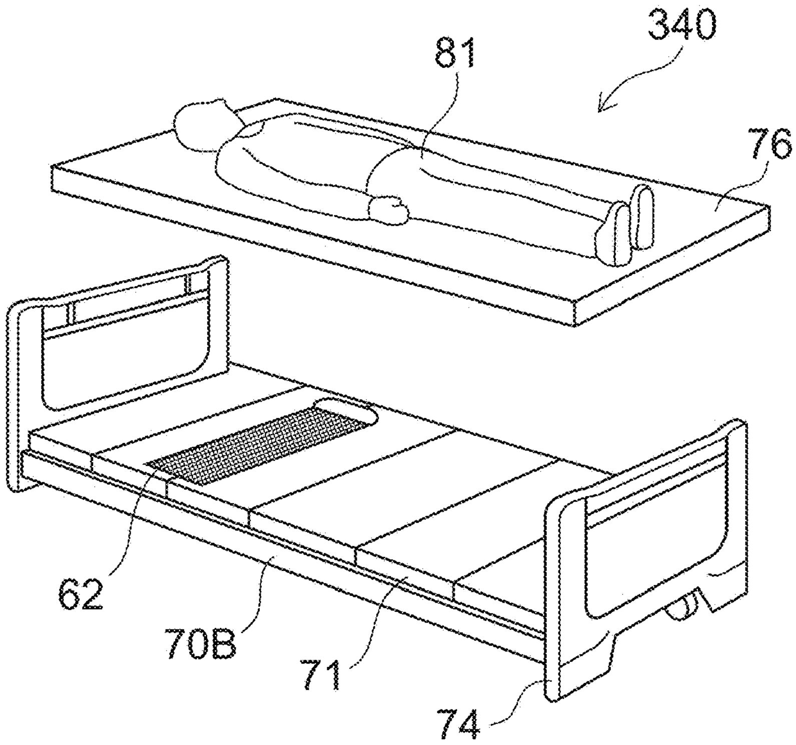
FIG. 16A and FIG. 16B are schematic views illustrating the motorized furniture according to the embodiment.
Figure 16B:
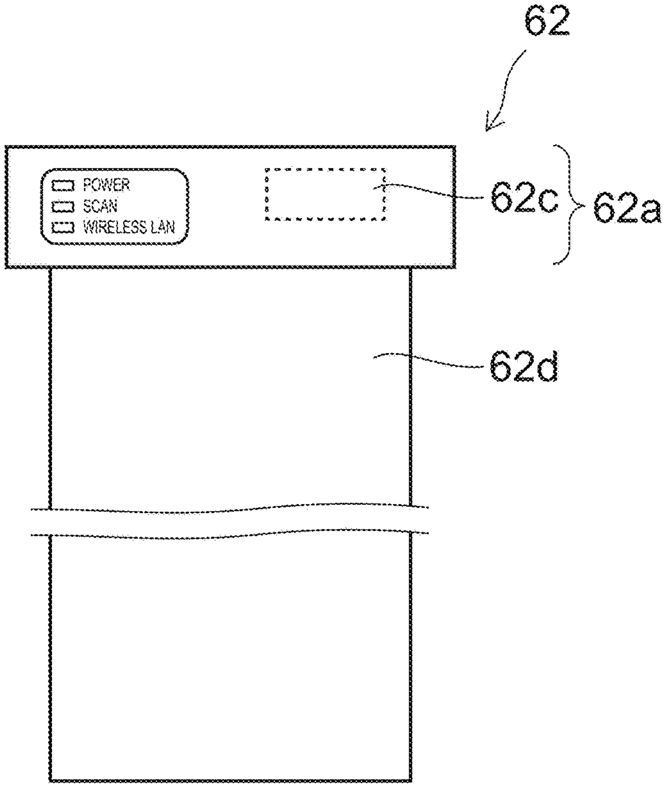

FIG. 16A and FIG. 16B are schematic views illustrating the motorized furniture according to the embodiment.

FIG. 16A is a schematic perspective view illustrating the sleep sensor 62 and the arrangement of the sleep sensor 62. FIG. 16B is a schematic plan view illustrating the sleep sensor 62. In FIG. 16A, the components are drawn apart from each other for clarity of illustration.

As shown in FIG. 16A, in the motorized furniture 340, the bottom 71 is provided on a bed leg part 74 of a bed part 70B. The mattress 76 is provided on the bottom 71. A user 81 lies on the mattress 76. The sleep sensor 62 is provided between the bottom 71 and the mattress 76. In this example, the sleep sensor 62 is sheet-shaped or plate-shaped.

As shown in FIG. 16B, the sleep sensor 62 includes a circuit 62*a* and the sensor 62*d*. The circuit 62*a* includes a communicator 62*c*. The communicator 62*c* transmits and receives data to and from the processor 43. Transmission and reception may be by any method including wired and/or wireless.

The sensor 62*d* detects, for example, a force (or a characteristic corresponding to the force) that the sensor 62*d* receives. The force includes, for example, at least one of pressure and/or sound wave. The sensor 62*d* includes, for example, a pressure sensor. The sensor 62*d* includes, for example, a microphone.

The force (at least one of pressure and sound wave) by the user 81 is applied to the sensor 62*d* via the mattress 76. For example, a signal based on the force detected by the sensor 62*d* is output from the circuit 62*a*. The output signal is supplied to the processor 43. In the processor 43, the state of the user 81 (getting out of bed, sleeping, waking, etc.) is estimated based on at least one of the magnitude of the signal (force) and the temporal change in the magnitude of the signal (force). Alternatively, in the circuit 62*a*, the state of the user 81 (getting out of bed, sleeping, or waking) may be estimated based on at least one of the force detected by the sensor 62*d* and the temporal change in the force. The state of the user 81 may include getting up, preparing to get out of bed (for example, sitting on the edge), getting out of bed, falling asleep, sleeping, or waking up.

Furthermore, in at least one of the processor 43 and the circuit 62*a*, the biological signal of the user is detected based on at least one of the magnitude of the signal (force) and the temporal change in the magnitude of the signal (force). The biological signal includes at least one of the user's breathing rate and heart rate. A state of sleep may be estimated based on the biological signal. The user's posture while sleeping may be estimated based on the biological signals.

For example, vibration according to the state of the user 81 is applied to the sensor 62*d*. The vibration corresponds to the body movement of the user 81, for example. The vibration is detected at the sensor 62*d*. The vibration may include sound.

For example, vibration detection means (sensor 62*d*) and processor (at least a part of at least one of circuit 62*a* and processor 43) are provided. The processor includes, for example, a computer. The vibration detection means detects, for example, the vibration of the sleeping person (user 81) on the bedding (bed part 70B).

The processor includes, for example, activity amount calculation means, sleep determination value calculation means, and sleep state determination means. These means are functionally separated. The activity amount calculation means calculates the activity amount of the sleeping person for each sampling unit time, for example, based on the vibration detected by the vibration detection means. The sleep determination value calculation means weights, for example, the amount of activity at a first time (for example, the current time) and the amount of activity calculated at a second time (for example, a time before the current time) according to time. The sum of the values multiplied by the correction coefficients may be calculated as the sleep determination value. For example, the sleep state determining means may determine that the user is in the awake state when the sleep determination value exceeds a predetermined threshold, and otherwise determine that the user is in a sleeping state.

FIG. 17A to FIG. 17D are schematic views illustrating another motorized furniture according to the embodiment.

Figure 17A:
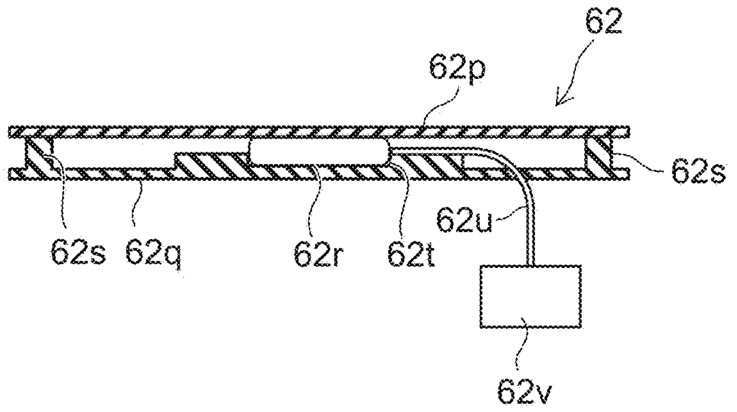
FIG. 17A to FIG. 17D are schematic views illustrating another motorized furniture according to the embodiment.
Figure 17B:
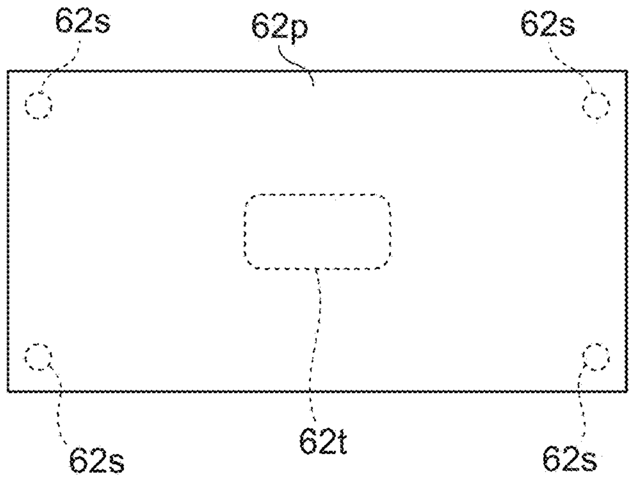
Figure 17C:
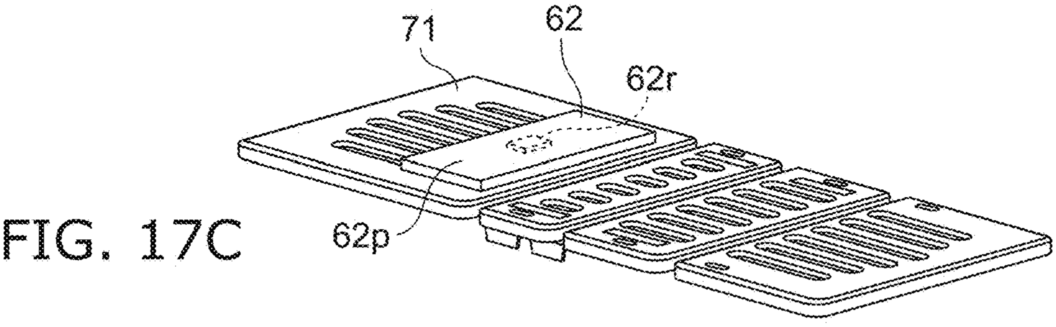
Figure 17D:
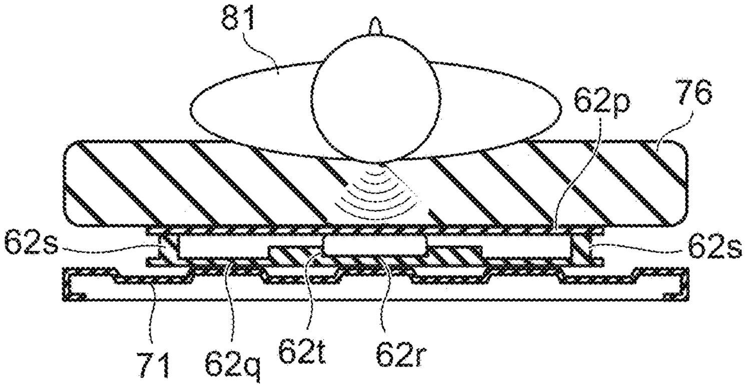

FIG. 17A is a cross-sectional view of another example of the sleep sensor 62. FIG. 17B is a plan view of an example of the sleep sensor 62. FIG. 17C is a perspective view illustrating the arrangement of the sleep sensor 62. FIG. 17D is a side view illustrating the arrangement of the sleep sensor 62.

As shown in FIG. 17A, in this example, the sleep sensor 62 includes a first plate 62*p* and a second plate 62*q*. The second plate 62*q* faces the first plate 62*p*. These plates may be sheet-like.

The second plate 62*q* includes support protrusions 62*s*. The support protrusions 62*s* oppose an outer edge part of the first plate 62*p*. The first plate 62*p* includes an inner part inside the outer edge part. An air container 62*r* is provided between the inner part and the second plate 62*q*. In this example, a groove 62*t* is provided in the second plate 62*q*. The air container 62*r* is provided in a space (divided space) formed by the groove 62*t*. One end of a signal line 62*u* is connected to the air container 62*r*. The other end of the signal line 62*u* is connected to a detection circuit 62*v* (detection device).

As shown in FIG. 17B, the support protrusion 62*s* faces a part of the outer edge of the first plate 62*p*. In this example, the support protrusions 62*s* are provided at four corners of the first plate 62*p*. The sleep sensor 62 is sheet-like or plate-like.

As shown in FIG. 17C, the sleep sensor 62 is placed on the bottom 71.

As shown in FIG. 17D, the sleep sensor 62 is placed on the bottom 71, and the mattress 76 is placed thereon. The user 81 lies on the mattress 76.

For example, a force according to the movement of the body of the user 81 is applied to the air container 62*r*. This force includes, for example, vibration. A force (or characteristic corresponding to the force) applied to the air container 62*r* is detected by the detection circuit 62*v*. For example, the air container 62*r* is provided with a pressure detector, and a signal (detection result) obtained by the pressure detector is supplied to the detection circuit 62*v*. For example, the air container 62*r* is provided with a microphone, and a signal (detection result) obtained by the microphone is supplied to the detection circuit 62*v*. For example, the output (signal) of the detection circuit 62*v* is supplied to the processor 43. The processor 43 estimates the state of the user 81 (getting out of bed, sleeping, awake, or the like). Alternatively, the detection circuit 62*v* may estimate the state of the user 81 (getting out of bed, sleeping, wakefulness, etc.) based on at least one of the detected force and temporal change in the force. The state of the user 81 may include sitting up, sitting on the edge (for example, preparing to get out of bed), getting out of bed, falling asleep, sleeping, or waking up.

The sleep sensor 62 is, for example, a biological information collecting device. In the sleep sensor 62, the first plate 62*p* is arranged on the body side of the user 81, for example.

The second plate 62*q* is provided, for example, on the support side. The deformable air container 62*r* for air pressure detection is provided between the central part of the first plate 62*p* and the second plate 62*q*. The groove 62*t* for mounting the air container 62*r* is provided in the central part of the second plate 62*q*. The support protrusions 62*s* protrude in a direction which goes to the first plate 62*p* from the second plate 62*q*. The support protrusions 62*s* support the four corners around the first plate 62*p*. The support protrusions 62*s* always support the first plate 62*p* in a horizontal state (normal state), for example.

In the embodiment, the sleep sensor 62 can be modified in various ways.

Figure 18:
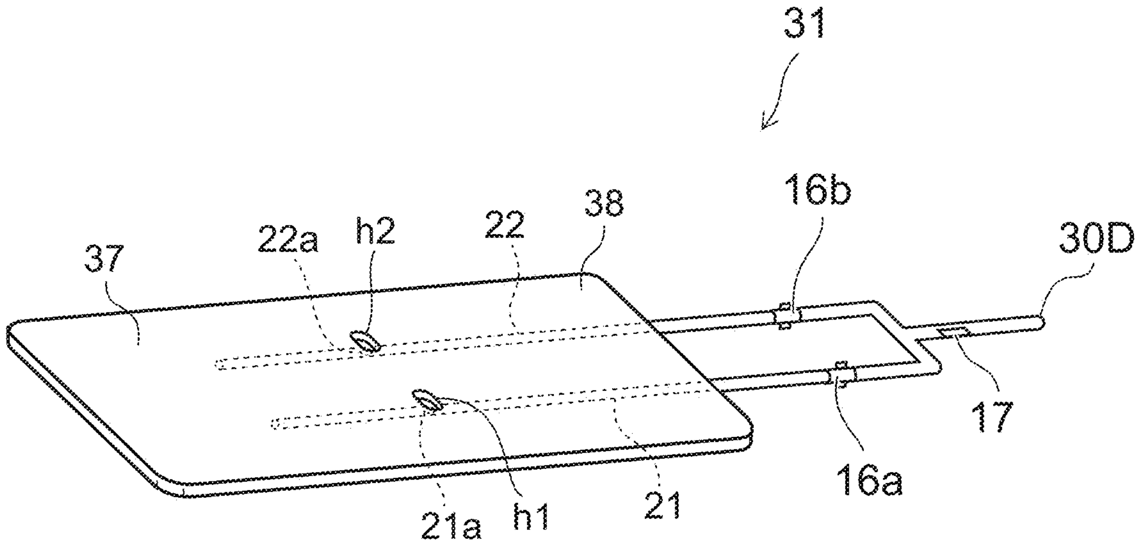
FIG. 18 is a schematic perspective view illustrating the excretion sensor according to the embodiment.

FIG. 18 is a schematic perspective view illustrating the excretion sensor according to the embodiment.

As shown in FIG. 18, the excretion sensor 31 includes the gas collector 38. The gas collector 38 includes a seat part 37 and tubes (first tube 21 and second tube 22 in this example). The seat part 37 is provided with holes (for example, first hole h1 and second hole h2). For example, the first tube 21 is provided with a first opening 21*a*. The second tube 22 is provided with a second opening 22*a*. For example, the first hole h1 overlaps the first opening 21*a*. For example, the second hole h2 overlaps the second opening 22*a*.

A first pump 16*a* is provided at the end of the first tube 21. A second pump 16*b* is provided at the end of the second tube 22. The odor sensor 17 is provided on a drain side of these pumps. These pumps suck the gas in the vicinity of the first hole h1 and the second hole h2 through these tubes. For example, the user's buttocks (e.g., a diaper, etc.) are located near these holes. When the user excretes, the gas including the odor associated with excretion is sent to the odor sensor 17 through the tube. When this odor is detected by the odor sensor 17, excretion is detected. The sucked gas is discharged from an exhaust port 30D.

In the embodiment, the configuration of the excretion sensor (excretion sensor 31) can be modified in various ways.

Two or more of the multiple embodiments described above may be arbitrarily combined within a technically possible range.

According to the information providing device and the motorized furniture according to the embodiment, the burden on caregivers can be reduced. For example, the user's QOL can be improved.

The embodiment may include the following configuration (draft).

Configuration 1

An information providing device, comprising:

a processor, the processor that acquires a first signal and a second signal, the first signal being obtained from an excretion sensor to detect excretion of a user, the second signal being obtained from a sleep sensor to detect a sleep state of the user, the processor outputting a notification signal for notifying the excretion when the first signal includes first information corresponding to a fact that the user is excreting and the second signal includes second information corresponding to a fact that the user is awake, the processor not outputting the notification signal in a first mode, when the first signal includes the first information and, the second signal does not include the second information.

Configuration 2

An information providing device, comprising:

a processor, the processor that acquires a first signal and a second signal, the first signal being obtained from an excretion sensor to detect excretion of a user, the second signal being obtained from a sleep sensor to detect a sleep state of the user, the processor outputting a notification signal for notifying the excretion when the first signal includes first information corresponding to a fact that the user is excreting feces and the second signal includes second information corresponding to a fact that the user is awake, the processor not outputting the notification signal in a first mode, when the first signal includes the first information and, the second signal does not include the second information.

Configuration 3

An information providing device, comprising:

a processor, the processor that acquires a first signal and a second signal, the first signal being obtained from an excretion sensor to detect excretion of a user, the second signal being obtained from a sleep sensor to detect a sleep state of the user, the processor outputting a notification signal for notifying the excretion when the first signal includes first information corresponding to a fact that the user is excreting urine and the second signal includes second information corresponding to a fact that the user is awake, the processor not outputting the notification signal in a first mode, when the first signal includes the first information and, the second signal does not include the second information.

Configuration 4

The information providing device according to any one of Configurations 1 to 3, wherein the processor outputs the notification signal in a second mode, when the first signal includes the first information.

Configuration 5

An information providing device, comprising:

a processor, the processor that acquires a first signal and a second signal, the first signal being obtained from an excretion sensor to detect excretion of a user, the second signal being obtained from a bed-departure sensor detect bed-departure of the user, the processor outputting notification signal for notifying the excretion when the first signal includes first information that the user is excreting and the second information includes information that the user is on a bed, the processor not outputting the notification signal, when the first signal includes the first information and the second signal includes information that the user is bed-departing.

Configuration 6

An information providing device, comprising:

a processor, the processor operating a device for the user when obtaining a received signal corresponding to receiving a notification signal transmitted based on a detection result by an excretion sensor to detect excretion of a user.

Configuration 7

The information providing device according to Configuration 6, wherein the device includes a motorized furniture used by the user.

Configuration 8

The information providing device according to Configuration 6, wherein the device includes a motorized bed used by the user, and the processor raises a height of a bottom of the motorized bed when receiving the received signal.

Configuration 9

The information providing device according to Configuration 6, wherein the device includes a motorized bed used by the user, and the processor flattens a bottom of the motorized bed when receiving the received signal.

Configuration 10

The information providing device according to Configuration 6, wherein the device includes an air mattress used by the user, and the processor stiffens the air mattress when receiving the received signal.

Configuration 11

The information providing device according to Configuration 6, wherein the device includes a lighting, and the processor brightens the lighting when receiving the received signal.

Configuration 12

The information providing device according to any one of Configurations 6 to 11, wherein the processor outputs a notification signal for notifying the excretion when receiving the received signal.

Configuration 13

An information providing device, comprising:

a processor, when the processor acquires a signal obtained from a position sensor to detect a position of a user and the position of the user is not in a state where excretion is detected by an excretion sensor, the processor notifying the state.

Configuration 14

The information providing device according to Configuration 13, wherein the position sensor includes a load sensor.

Configuration 15

An information providing device, comprising:

a processor configured to detect excretion of a user based on first information and second information, the first information including detection result of odor obtained from a space around the user, and the second information including at least one of biological information of the user or motorized furniture information relating to a state of a motorized furniture used by the user.

Configuration 16

The information providing device according to Configuration 15, wherein the biological information includes at least one of sleep/awake of the user, body movement of the user, heart rate of the user, breathing rate of the user, bed-departure of the user, or being in bed of the user.

Configuration 17

The information providing device according to Configuration 15 or 16, wherein the motorized furniture includes a bottom, and the motorized furniture information includes at least one of an angle of the bottom or a height of the bottom.

Configuration 18

An information providing device, comprising:

a processor configured to output notification signal for notifying the excretion based on a signal obtained from an excretion sensor to detect odor obtained from a space around a user; and an excretion sensor controller configured to control operation of the excretion sensor, the excretion sensor controller being configured to receive an input relating to at least one of presence or absence of the excretion or diaper exchange.

Configuration 19

The information providing device according to Configuration 18, wherein the processor is configured to output an input received by the excretion sensor controller.

According to the embodiment, it is possible to provide an information providing device capable of more appropriately providing information on excretion.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in information providing devices or motorized furniture such as excretion sensors, sleep sensors, bed-departure sensors, load sensors, image sensors, movable parts, processors, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all information providing devices practicable by an appropriate design modification by one skilled in the art based on the information providing devices described above as embodiments of the invention also are within the scope of the invention to the extent that the spirit of the invention is included.

Various other variations and modifications can be conceived by those skilled in the art within the spirit of the invention, and it is understood that such variations and modifications are also encompassed within the scope of the invention.

EXPLANATION OF LETTERS OR NUMERALS

16*a* 16*b* first, second pump, 17 odor sensor, 21, 22 first, second tube, 21*a*, 22*a* first, second opening, 30D exhaust port, 31 excretion sensor, 31*a* circuit, 31*c* communicator, 31*d* sensor, 31*r* excretion sensor controller, 31*ra*, 31*rb* button, 37 seat part, 43 processor, 47 bad side terminal, 61 bed-departure sensor, 61F load sensor, 61G image sensor, 61R body pressure measurement mat, 61S position sensor, 62 sleep sensor, 62*a* circuit, 62*c* communicator, 62*d* sensor, 62*p*, 62*q* first, second plate, 62*r* air container, 62*s* support protrusion, 62*t* groove, 62*u* signal line, 62*v* detection circuit, 63 server, 64 communicator, 70 movable part, 70B bed part, 70*a* back bottom, 70*b* knee bottom, 70*c* leg bottom, 70*d* head bottom, 70*g* caster, 70*h* height change part, 70*r* control device, 70*ra* user interface device, 70*rb* cable, 71 bottom, 74 bed leg part, 75 frame, 76 mattress, 76*a* air mattress, 76*b* air cell, 76*c* pump unit, 76*p*, 76*q* cable, 76*r* air mattress controller, 76*s* seat, 77 lighting, 81 user, 110, 120, 130, 140, 150, 160 information providing device, 310, 320, 330, 340, 350, 360 motorized furniture, H1 height, IN1, IN2 first, second information, MD1, MD2 first, second mode, Sg1, Sg2 first, second signal, Sga notification signal, h1, h2 first, second hole

The invention claimed is:

1. An information providing device, comprising:

a processor, the processor that acquires a first signal and a second signal, the first signal being obtained from an excretion sensor to detect excretion of urine or feces of a user, the second signal being obtained from a sleep sensor to detect a sleep state of the user, the processor outputting a notification signal for notifying the excretion of urine, when the first signal includes first information corresponding to a fact that the user is excreting urine, and the second signal includes second information corresponding to a fact that the user is awake, the processor not outputting the notification signal in a first mode, when the first signal includes the first information corresponding to a case where the user is excreting urine and, the second signal does not include the second information, and outputs a notification signal for notifying that the user is excreting feces when the first signal includes first information corresponding to a case where the user is excreting feces regardless of whether the second signal includes the second information.

2. The information providing device according to claim 1 wherein the processor operates a device for the user when obtaining a received signal corresponding to a notification signal transmitted based on a detection result by an excretion sensor to detect excretion of a user.

3. The information providing device according to claim 2, wherein the device includes a motorized furniture used by the user.

4. The information providing device according to claim 2, wherein the device includes a motorized bed used by the user, and the processor raises a height of a bottom of the motorized bed when receiving the received signal.

5. The information providing device according to claim 2, wherein the device includes a motorized bed used by the user, and the processor flattens a bottom of the motorized bed when receiving the received signal.

6. The information providing device according to claim 2, wherein the device includes an air mattress used by the user, and the processor stiffens the air mattress when receiving the received signal.

7. The information providing device according to claim 2, wherein the device includes a lighting, and the processor brightens the lighting when receiving the received signal.

8. The information providing device according to claim 1, wherein, when the processor acquires a signal obtained from a position sensor to detect a position of a user and the position of the user is not in a state where excretion is detected by an excretion sensor, the processor notifies the state.

9. The information providing device according to claim 8, wherein the position sensor includes a load sensor.

10. The information providing device according to claim 1, wherein, the processor is further configured to detect excretion of a user based on first information and second information, the first information includes a detection result of odor obtained from a space around the user, and the second information includes at least one of biological information of the user or motorized furniture information relating to a state of a motorized furniture used by the user.

11. The information providing device according to claim 10, wherein the biological information includes at least one of sleep/awake of the user, body movement of the user, heart rate of the user, breathing rate of the user, bed-departure of the user, or being in bed of the user.

12. The information providing device according to claim 10, wherein the motorized furniture includes a bottom, and the motorized furniture information includes at least one of an angle of the bottom or a height of the bottom.

13. The information providing device according to claim 1, further comprising:

an excretion sensor to detect odor obtained from a space around a user; and an excretion sensor controller configured to control operation of the excretion sensor, the excretion sensor controller being configured to receive an input relating to at least one of presence or absence of the excretion or diaper exchange.

14. The information providing device according to claim 13, wherein the processor is configured to output an input received by the excretion sensor controller.

* * * * *